(12) United States Patent
Purdy et al.

(10) Patent No.: US 7,795,878 B2
(45) Date of Patent: Sep. 14, 2010

(54) DIMENSIONS DETERMINATION FOR INSULATING COATINGS

(75) Inventors: Aaron T. Purdy, Marysville, WA (US); Theresa N. Ward, Redmond, WA (US); J. Sidney Clements, Boone, NC (US); Michael G. Anderson, Renton, WA (US); Julie K. Bennett, Bellevue, WA (US)

(73) Assignee: The Boeing Company, Chicago, IL (US)

( * ) Notice: Subject to any disclaimer, the term of this patent is extended or adjusted under 35 U.S.C. 154(b) by 388 days.

(21) Appl. No.: 11/876,574

(22) Filed: Oct. 22, 2007

(65) Prior Publication Data
US 2009/0102486 A1    Apr. 23, 2009

(51) Int. Cl.
*G01N 27/60*    (2006.01)
*H01H 31/12*    (2006.01)
(52) U.S. Cl. .................. 324/536; 324/452; 324/551
(58) Field of Classification Search .............. 324/72, 324/72.5, 536, 551, 554, 452–458
See application file for complete search history.

(56) References Cited

U.S. PATENT DOCUMENTS

| | | | |
|---|---|---|---|
| 3,156,866 A * | 11/1964 | Anderson et al. ............ 324/72 |
| 3,760,262 A * | 9/1973 | Chovanec et al. ........... 324/452 |
| 3,906,308 A | 9/1975 | Amason et al. |
| 4,352,142 A * | 9/1982 | Olson ......................... 361/218 |
| 4,583,702 A | 4/1986 | Baldwin |
| 4,912,594 A * | 3/1990 | Bannink et al. ............. 361/218 |
| 7,186,280 B2 * | 3/2007 | Eom et al. .................. 29/25.01 |
| 2005/0213278 A1 * | 9/2005 | Hawley ....................... 361/212 |
| 2006/0051592 A1 * | 3/2006 | Rawlings et al. ......... 428/423.1 |
| 2006/0146473 A1 * | 7/2006 | Heidlebaugh et al. ....... 361/220 |

* cited by examiner

*Primary Examiner*—Timothy J Dole
*Assistant Examiner*—Farhana Hoque
(74) *Attorney, Agent, or Firm*—Lee & Hayes, PLLC (57) ABSTRACT

Systems and methods for determining the dimensions of insulating coating sections applied to a conductive component are disclosed. The method includes providing a specimen having an insulating coating section of a first surface area and a first thickness. The method further includes conducting a test of the specimen for propagating brush discharges. If the specimen exhibits propagating brush discharges, the method further includes reducing at least one of the first surface area and the first thickness to produce at least one of a second surface area or a second thickness, or reducing a first maximum distance that any portion of the insulating coating may extend from an adjacent static dissipative feature to produced a second maximum distance. In additional embodiments, insulating coating patterns may be established on the component based on at least one of the dimensions of the second surface area, the second thickness, or the second maximum distance.

18 Claims, 9 Drawing Sheets

DIMENSIONS DETERMINATION FOR INSULATING COATINGS

CROSS REFERENCE TO RELATED APPLICATIONS

This patent application is related to the following co-pending, commonly-owned U.S. patent application, which application is hereby incorporated by reference: U.S. patent application Ser. No. 11/764,077 entitled "Application of Insulating Coating".

TECHNICAL FIELD

The present disclosure relates to systems and methods for providing electrical insulation, and more specifically, to systems and methods for applying electrical insulation in a manner that prevents electrical surface discharges.

BACKGROUND

The application of thin insulating coatings onto conductive materials is common in a variety of industries. In some instances, these insulating coatings may be purposefully applied to mitigate or prevent the corrosive degradation of the conductive materials. For example, insulating coatings may mitigate or prevent galvanic corrosion of metallic aircraft components by preventing charge mobility between components. In other instances, the insulating coatings may be applied to enhance the adhesion of subsequently applied coatings or materials, protect the substrate from harmful radiation exposure (e.g., ultraviolet emissions), act as a light reflective material, and retard microbial growth. Moreover, in additional instances, purely cosmetic coatings applied to conductive materials may also act as unintended insulating coatings. This is often due to the fact that cosmetic coatings rarely have electrostatic requirements.

The combination of insulating coating on electrically-grounded conductive materials, or substrates, may create capacitance as electrostatic charges accumulate on the coating surfaces. Capacitance may result in spontaneous, self-initiated electrical surface discharges when the electrostatic charges cannot relax to ground. These spontaneous, self-initiated electrical surface discharges are also commonly known as propagating brush discharges (PBD). Propagating brush discharges are undesirable. Cosmetic coatings may be made conductive to mitigate or eliminate such electrical surface discharges. However, conductive coatings cannot be substituted for insulating coatings that prevent galvanic corrosion.

SUMMARY

Systems and methods for determining the dimensions of insulating coating sections applied to a conductive component are disclosed. These novel systems and methods provide insulating coating applications that do not compromise the galvanic protection and other useful functions of the insulating coating, yet advantageously reduce or eliminate the possibility of electrical surface discharges. Embodiments of systems and methods in accordance with the present disclosure may advantageously provide dimensioned insulating coating sections on the conductive component. The dimensioned insulating coating sections generally results in bare conductive surface sections of the conductive component that reduce or eliminate electrical surface discharges, also known as propagating brush discharges (PBD). In some instances, the dimensioned insulating coating sections may also prevent galvanic corrosion between the conductive component and other galvanically incompatible conductive components by enabling maximum insulating coating application.

In one embodiment, a method for mitigating propagating brush discharges from an insulating coating covered component includes providing a specimen of the component for testing. The specimen having an insulating coating section of a first surface area and a first thickness. The method further includes conducting a test of the specimen for propagating brush discharges. If the specimen exhibits propagating brush discharges, the method further includes reducing at least one of the first surface area or the first thickness to produce a second surface area and a second thickness, or reducing a first maximum distance that any portion of the insulating coating may extend from an adjacent static dissipative feature to produced a second maximum distance. In additional embodiments, insulating coating patterns may be established on the component based on at least one of the dimensions of the second surface area, the second thickness, or the second maximum distance.

In other embodiments, the method for mitigating propagating brush discharges includes a method that tests for propagating brush discharge testing. The test method includes preparing component specimen for propagating brush discharge testing, wherein the component specimen has an insulating coating. The method includes first providing an electrical charge to the component specimen. Second, the component specimen is discharged to a ground, which causes propagating brush discharges (PBD) to occur. Third, the method includes determining the occurrence of propagating brush discharges based on the one or more patterns produced by the discharge of the component specimen to the ground.

In additional embodiments, a system for propagating brush discharge testing includes a voltage supply configured to provide a large charging electrical potential. The system also includes a corona charger configured to apply the charging voltage to a component relative to a ground for the component. The component has an insulating coating. The system further includes a discharge probe configured to discharge an electrical charge from the component. An image recorder configured to capture one or more patterns produced by the discharge of the component to a ground is also included in the system. In a specific embodiment, the system further includes a measurement device configured to measure the charge transfer to the discharge probe.

The features, functions, and advantages that have been discussed above or will be discussed below can be achieved independently in various embodiments, or may be combined in yet other embodiments, further details of which can be seen with reference to the following description and drawings.

BRIEF DESCRIPTION OF THE DRAWINGS

Embodiments of systems and methods in accordance with the teachings of the present disclosure are described in detail below with reference to the following drawings.

DETAILED DESCRIPTION

Embodiments of systems and methods in accordance with the present disclosure are directed to determining the dimensions of insulating coating sections that are applied to electrically-grounded conductive components. These electrically-grounded components may include, for example, carbon fiber reinforced plastic (CFRP) aircraft components. The application of an insulating coating to a surface of a conductive component in properly dimensioned sections leaves other sections of the conductive component free of the insulation coating and electrically conductive. Accordingly, the accumulation of undesirable quantities of electrostatic charges, which may result in propagating brush discharges (PBD) on the insulating coating surface, may be prevented. In this way, electrical surface discharges from conductive components are mitigated. Many specific details of certain embodiments are set fourth in the following description and in FIGS. 1-8 to provide a thorough understanding of such embodiments. The present disclosure may have additional embodiments, or may be practiced without one or more of the details described below.

Figure 1:
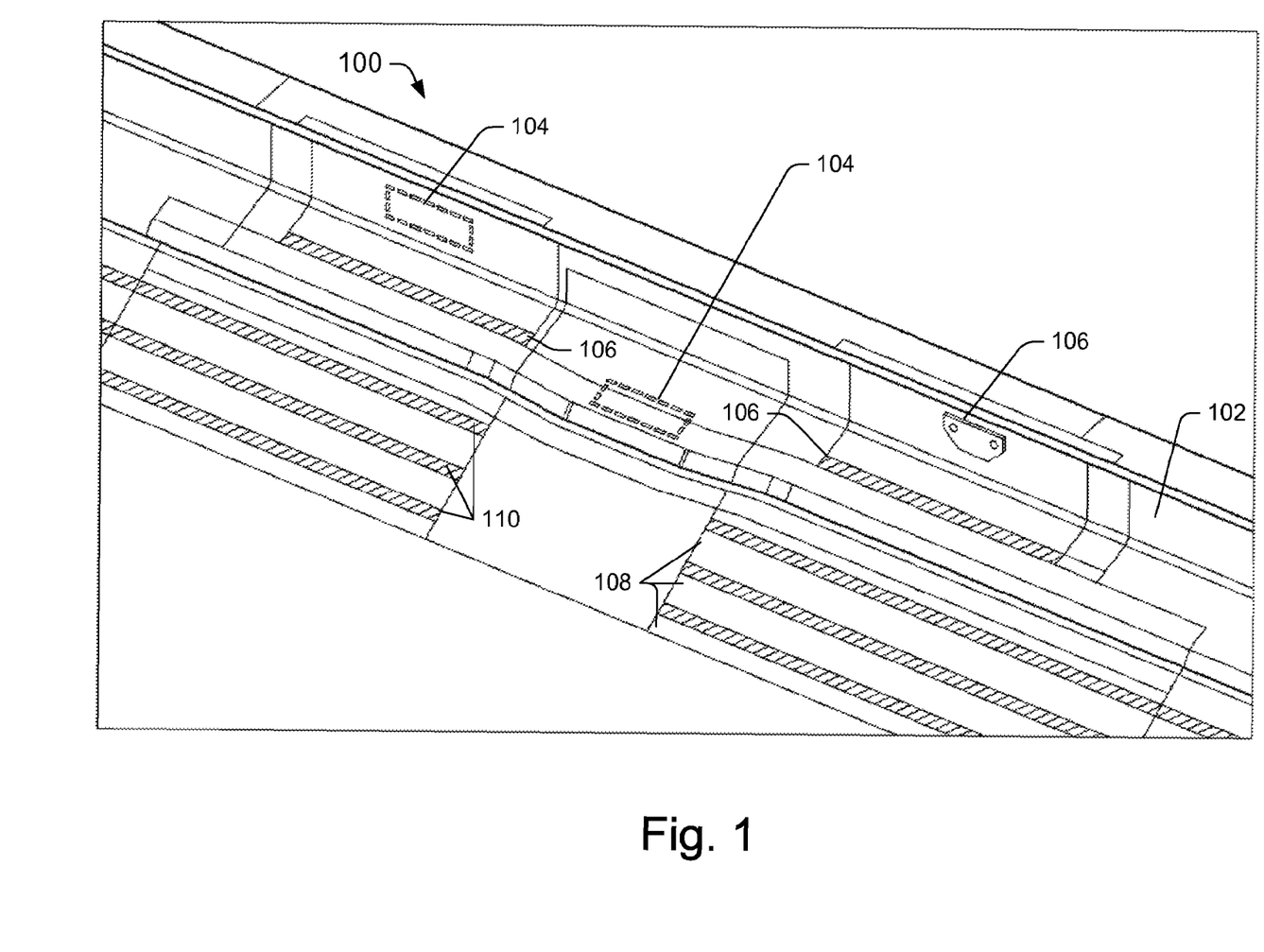
FIG. 1 is an isometric view of an exemplary carbon fiber reinforced plastic (CFRP) conductive component. The exemplary CFRP conductive component depicts a concept of applying an insulating coating to prevent electrical surface discharges, in accordance with an embodiment.

FIG. 1 is an isometric view of a sample carbon fiber reinforced plastic (CFRP) conductive component 100. Sample CFRP conductive component 100 illustrates an exemplary concept for applying an insulating coating in dimensioned sections to provide galvanic corrosion protection while preventing electrical surface discharges. The dimensions of the sections may be determined using methods that are further described below. In accordance with various implementations, the CFRP conductive component 100 may be manufactured from a CFRP designated as BMS 8-276 by the Boeing Company of Chicago, Ill.

The CFRP conductive component 100 may include a surface area 102. The surface area 102 may include a plurality of attachment footprints 104. The attachment footprints 104 may be disposed such that they contact one or more metallic structural members 106 (e.g., metallic brackets, metallic shear-ties, and the like). In this way, the attachment footprints 104 may enable the CFRP conductive component 100 to be attached to one or more metallic components present in an aircraft. In one instance, the metallic structural members may include aluminum components. However, it will be appreciated that the metallic component attachment footprints 104 may enable the CFRP conductive component 100 to be attached to components constructed from other types of conductive metal.

According to various implementations, an insulating coating may be applied to the surface area 102 in dimensioned sections. The insulating coating is applied to prevent galvanic corrosion of metallic structural members attached to the CFRP conductive component 100. In other instances, the insulating coating is also be applied to enhance the adhesion of subsequently applied coatings or materials, protect the substrate from harmful radiation exposure (e.g., ultraviolet emissions), act as a light reflective material, and retard microbial growth on the CFRP conductive component 100 and so on.

As illustrated in FIG. 1, the application of the insulating coating in dimensioned sections, such as the dimensioned sections 108, leaves one or more unprimed areas 110 on the CFRP conductive component 100. The unprimed areas 110 may enable the dissipation of charges from the surface of the insulating coating into the CFRP conductive component 100. In this way, the unprimed areas 110 may advantageously mitigate the build up of electrostatic charges in the coating-covered CFRP conductive component 100 that may initiate propagating brush discharges.

Figure 2:
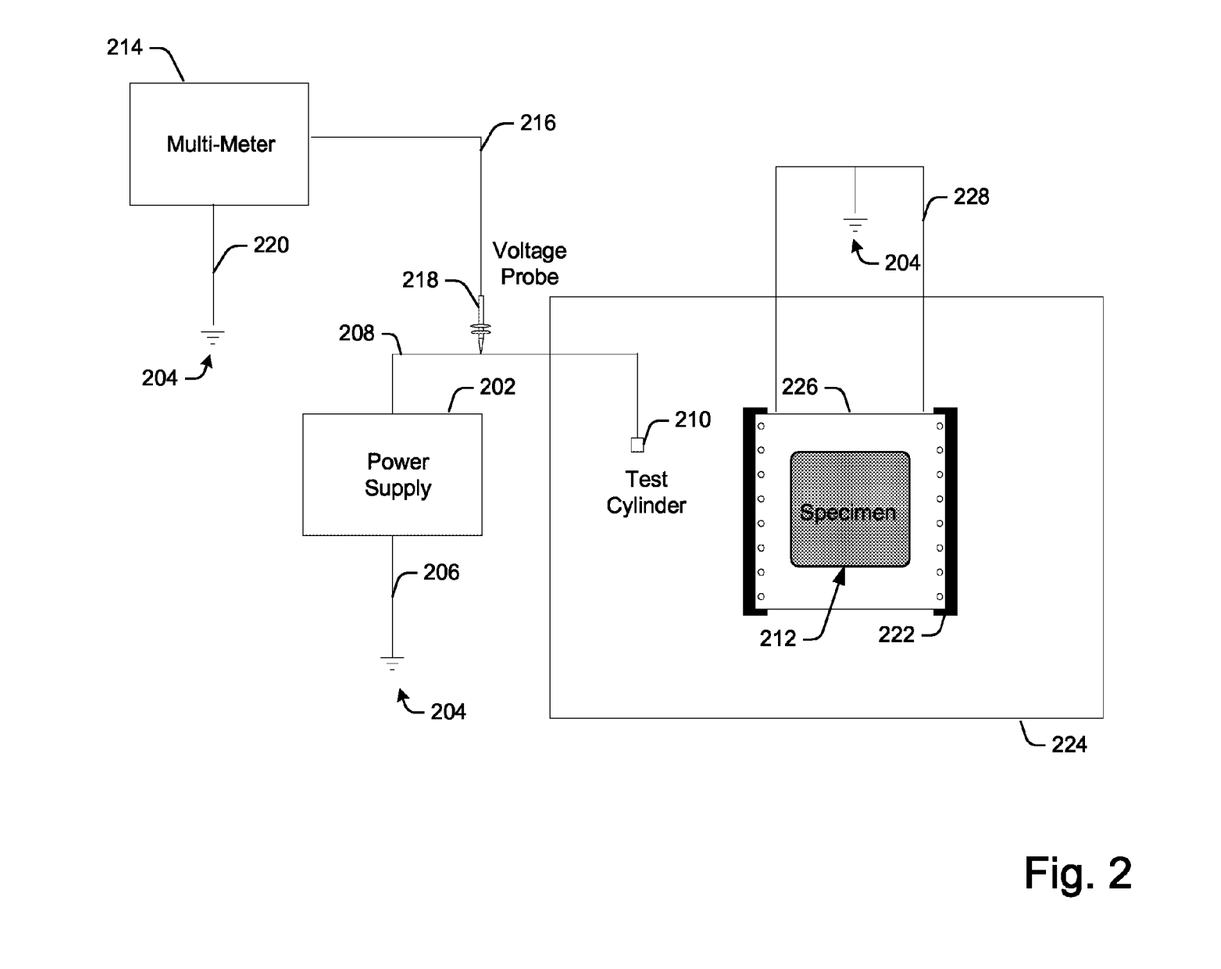
FIG. 2 is a partial schematic of an exemplary system for determining dielectric withstand voltage (DWV) in accordance with an embodiment.

FIG. 2 illustrates an exemplary system 200 for determining Dielectric Withstand Voltage (DWV) in accordance with an embodiment. The exemplary system 200 can be employed to facilitate the determination of insulating coating dimensions.

The system 200 includes a power supply 202. The power supply 202 is electrically connected to a ground 204 via one or more conductive leads 206. Additionally, the power supply 202 is also configured to supply an electrical potential via one or more conductive leads 208 to a test cylinder 210. In turn, the test cylinder 210 is configured to provide a removable, that is, interruptible electrical contact to a specimen 212. The system 200 further includes a multi-meter 214 for measuring Dielectric Withstand Voltage (DWV), According to various implementations, the multi-meter 214 may include one or more first conductive leads 216 that are electrically connected to a probe 218. The multi-meter 214 may also include one or more second conductive leads 220 that are connected to the ground 204. In this way, the multi-meter 214 may be configured to measure the electrical potential that is supplied to the specimen 212 when the probe 218 is brought into electrical contact with the one or more conductive leads 208 and the test cylinder 210 is in contact with the specimen 212

Figure 9:
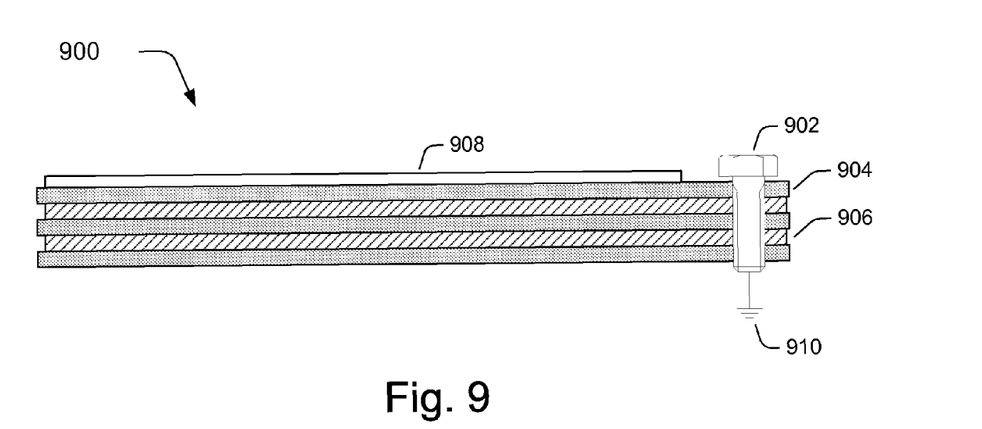
FIG. 9 is an enlarged side view of an exemplary carbon fiber reinforced plastic (CFRP) sample that is penetrated by a grounded fastener, in accordance with an embodiment.

The system 200 also includes a test bench 222. The test bench 222 may be enclosed in a chamber 224 that provides atmospheric isolation and humidity control capabilities. Additionally, the test bench 222 may be equipped with a conductive portion 226. The conductive portion 226 is configured to electrically contact the specimen 212. Moreover, the conductive portion 226 is also electrically connected, by one or more leads 228, to the ground 204 that is outside the chamber 224. Accordingly, the conductive portion 226 of the test bench 222 is configured to enable the flow of electrical current through the specimen 212 to the ground 204 in the event of an electrical breakdown in specimen 212. As further described below in FIG. 9, in instances where the specimen 212 is a multi-layered carbon fiber reinforced plastic (CFRP)

specimen that includes a top insulating coating, each of the conductive carbon fiber layers may be electrically grounded to the ground 204 via a penetrating conductive member (e.g., a metallic fastener).

In some implementations, the system 200 may be employed to conduct a Dielectric Withstand Voltage (DWV) test of an insulating coating covered conductive component according to ASTM D3755-97, entitled, "Standard Test Method for Dielectric Breakdown Voltage and Dielectric Strength of Solid Electrical Insulation materials Under Direct-Voltage Stress," (Reapproved 2004) as developed by ASTM International, and incorporated herein by reference.

Figure 3:
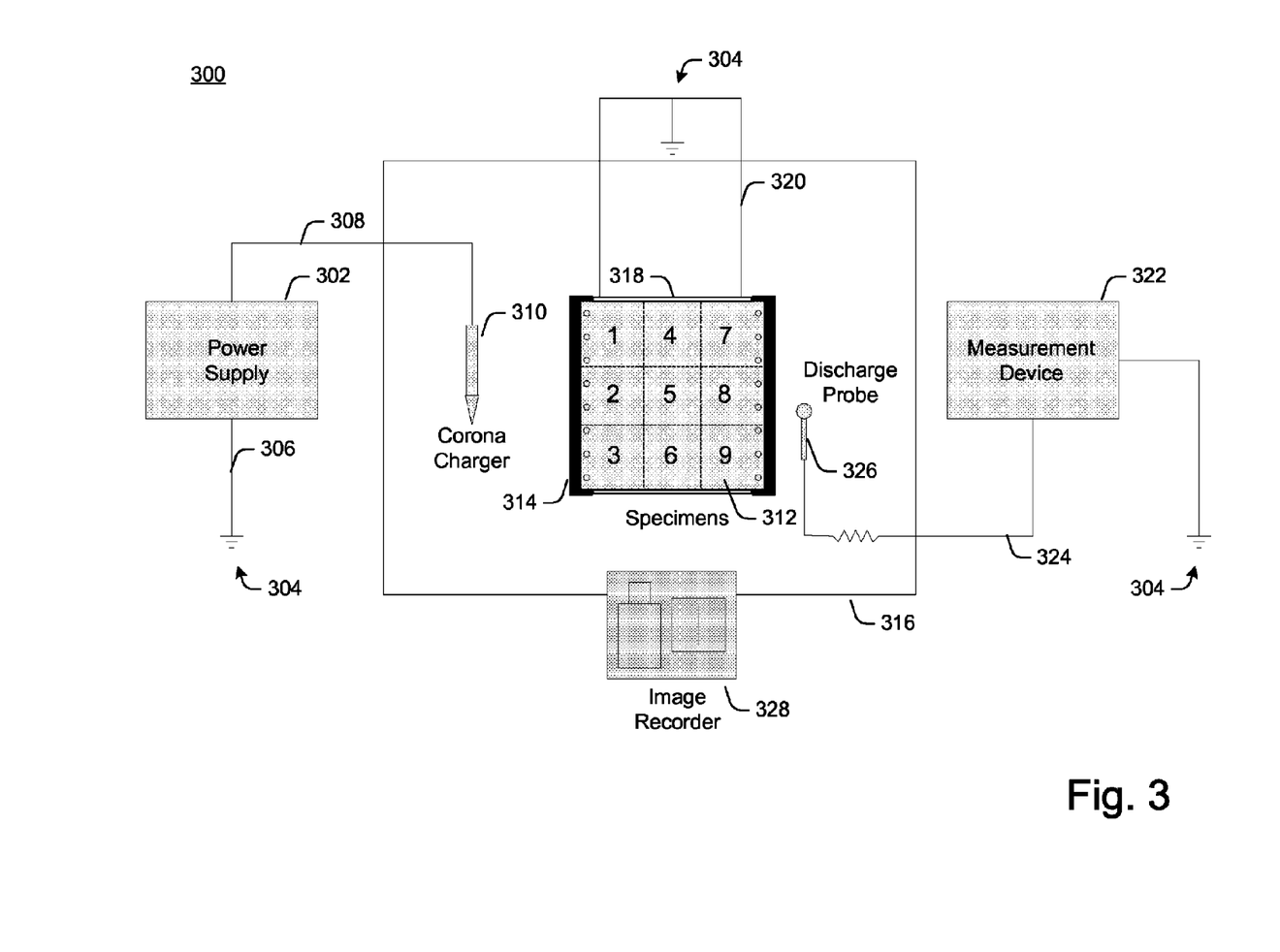
FIG. 3 is a partial schematic of an exemplary system for determining the occurrence of propagating brush discharges (PBD) in accordance with an embodiment.

FIG. 3 illustrates an exemplary system 300 for determining the occurrence of propagating brush discharges (PBD) in accordance with an embodiment. The exemplary system 300 can be employed to facilitate the determination of insulating coating dimensions.

The system 300 includes a power supply 302. The power supply 302 is electrically connected to a common ground 304 via one or more conductive leads 306. Additionally, the power supply 302 is also configured to supply an electrical potential (relative to the common ground 304) via one or more conductive leads 308 to a corona charger 310. In turn, the corona charger 310 is configured to deposit a charge on specimen 312.

The system 300 also includes a test bench 314. The test bench 314 may be enclosed in a chamber 316 that provides atmospheric isolation and humidity control capabilities. In this way, specimen 312 may be tested in a variety of atmospheric and humidity conditions. Additionally, the test bench 314 may be equipped with a conductive portion 318. The conductive portion 318 is configured to electrically contact the specimen 312. Moreover, the conductive portion 318 is also electrically connected, by one or more leads 320, to the common ground 304. Accordingly, the conductive portion 318 of the test bench 314 may give rise to a capacitance in the insulating coating on the specimen 312 via an electrical connection to the common ground 304.

Moreover, in instances where the specimen 212 is a multi-layered carbon fiber reinforced plastic (CFRP) specimen as described in FIG. 9, the conductive portion 318 of the test bench 314 may give a rise to a capacitance between all of the conductive carbon fiber layers and a top insulation coating, via an electrical connection to the common ground 304. In such instances, electrical connections between the common ground 304 and each of the conductive carbon fiber layers of the CFRP specimen may be established via a penetrating conductive member as further described with respect to FIG. 9.

The system 300 may further include a measurement device 322. The measurement device 322 may be an oscilloscope, an electrometer, or other electronic devices that are capable of quantifying charger transfer (e.g., integrating current or measuring charge). According to various implementations, the measurement device 322 may include one or more first conductive leads 324 that are electrically connected to a discharge probe 326. The measurement device 322 may also include one or more second conductive leads that are connected to the common ground 304. In this way, the measurement device 322 may be configured to measure the charger transfer that is discharged by the specimen 312 when the discharge probe 326 is brought into electrical contact with the specimen 312. In other words, the discharge probe 326 is configured to cause the specimen 312 to give propagating brush discharges (PBD) when it electrically contacts the specimen. However, it will be appreciated that in some embodiments, the measurement device 322 may be eliminated from system 300. In such embodiments, the discharge probe may be directly connected to the common ground 304 by the one or more first conductive leads 324. In some embodiments, the discharge probe should have a rounded smooth-shape end. For example, the rounded smooth-shaped end may be a sphere of between approximately 1 cm and 3 cm in diameter.

An image recorder 328 may be further included in the system 300. The image recorder 328 may be any device that is capable of recording a visual representation of a view for subsequent display. For example, the image recorder 328 may be a still-image camera, a motion video camera, or other types of cameras. In system 300, the image recorder 328 may be configured to record discharge patterns produced between the discharge probe 328 and the specimen 312.

FIGS. 4-7 illustrate exemplary processes for facilitating the determination of insulating coating dimensions. The order in which the operations are described in each process is not intended to be construed as a limitation, and any number of the described blocks can be combined in any order and/or in parallel to implement the process.

Figure 4:
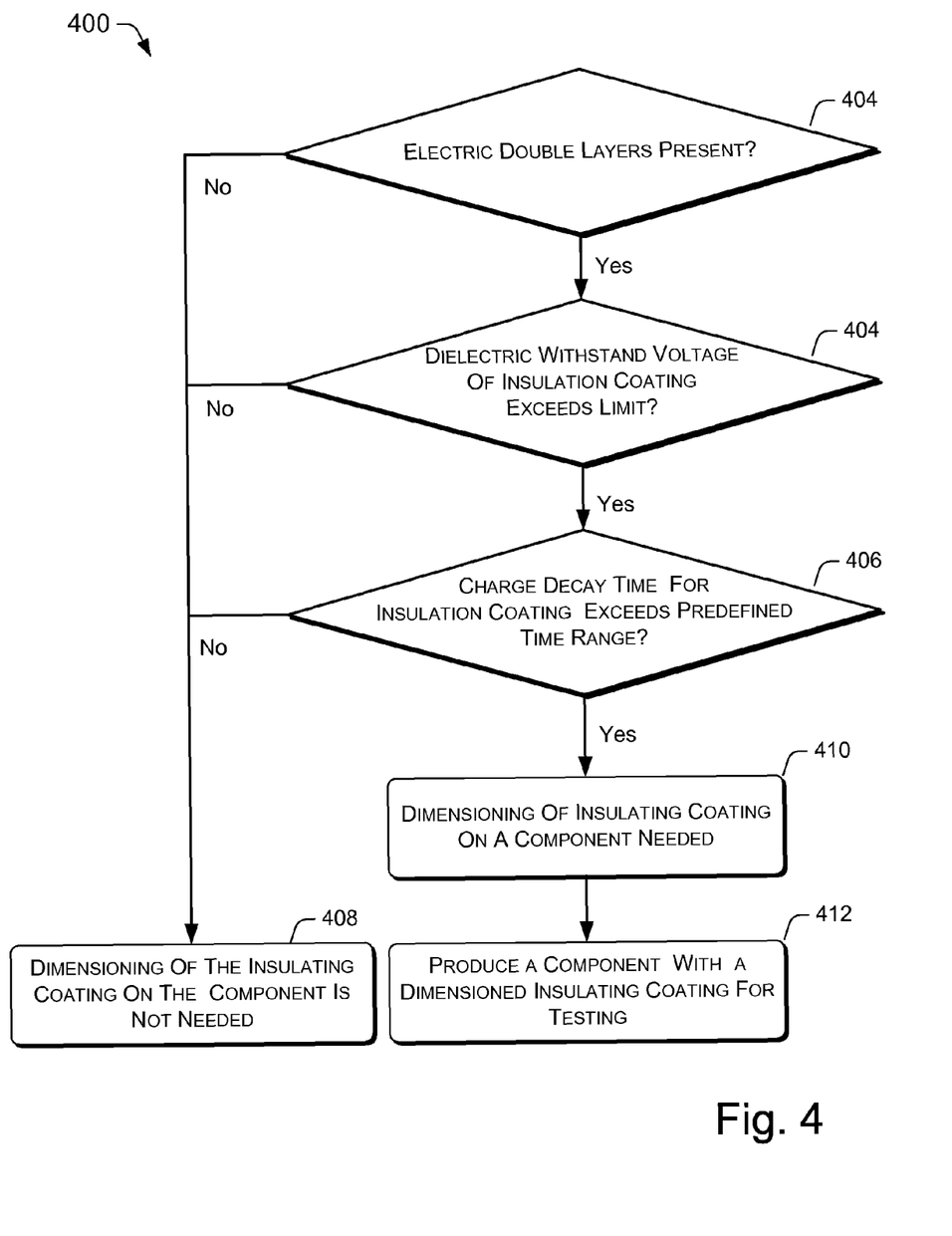
FIG. 4 is a flow diagram illustrating an exemplary process for determining whether the dimensioning of insulation coating on a conductive component is needed, in accordance with an embodiment.

FIG. 4 illustrates an exemplary process 400 for determining whether the dimensioning of insulation coating on a conductive component, is needed. In certain embodiments, the conductive component may be a carbon fiber reinforced plastic (CFRP) component. At decision block 402, a determination as to whether an "electric double layer" is present on the conductive component may be made. According to various embodiments, an "electric double layer" is considered present in instances where (1) the conductive component is grounded; (2) an insulating coating of a predetermined maximum thickness is applied to the grounded conductive component; and (3) the insulating coating is configured to separate the grounded conductive component from a source of electrostatic charge. In embodiments, the predetermined thickness of the insulating coating is less than approximately 8 to 10 (mm) millimeters at maximum total thickness. Moreover, the source of electrostatic discharge may include a charged fluid, a charged powder, as well as other sources that are capable of generating electrostatic charges. The presence of the "electric double layer" may cause the spontaneous initiation of propagating brush discharge.

Accordingly, if the "electric double layer" is not present for the conductive component ("no" at decision block 402), the process 400 may continue directly to block 408, where it is concluded that the dimensioning of the insulating coating on the conductive component is not needed. However, if an "electric double layer" is present for the conductive component ("yes" at decision block 402), the process may proceed to decision block 404.

At decision block 404, a determination as to whether the Dielectric Withstand Voltage (DWV) of the insulating coating on the conductive component exceeds a predetermined or desired DWV threshold may be made. In an embodiment, the DWV threshold is approximately 4 Kilovolts (kV), which is typical for most test materials. This determination may be accomplished by a DWV test. An exemplary DWV test is further illustrated in FIG. 5. If the DWV is not exceeded ("no" at decision block 404), the process 400 may yet again proceed directly to block 408, where it is concluded that the dimensioning of the insulating coating on the conductive component is not needed. However, if the DWV is exceeded ("yes" at decision block 404), the process 400 may advance to decision block 406.

At decision block 406, if the charge decay time constant on the insulating coating is within a predetermined time range, ("No" at decision block 406), the process 400 may once again proceed directly to block 408, where it is concluded that the dimensioning of the insulating coating on the conductive component is not needed. However, if it is determined that the insulating coating has a charge decay time constant that exceeds a predetermined time range, ("yes" at decision block 406), the process may proceed to block 410. At block 410, it is concluded that the dimensioning of the insulating coating on the conductive component is needed. According to various embodiments, the predetermined time range is approximately 1 second or less.

At block 410, one or more test samples, or component specimens, may be produced so that the conductive component with the insulating coating may be tested in a propagating brush discharge (PBD) testing system, such as the system 300 described in FIG. 3. For instance, a component specimen may be configured so that it is representative of the conductive component in its final implementation in terms of material of the component, dimensions of insulating coating present and static dissipative features present. Static dissipative features are those objects, surfaces, or protrusions that act as ground points or charge leakage paths. For example, static dissipative features may include other components with bare metal surfaces, bare fasteners, small "pin" holes in the insulating coating that expose conductive substrate, or any combination thereof. In instances, metal components and fasteners equipped with an insulating coating may also be capable of functioning as static dissipative feature as long as the metal component/insulating coating combination has a DWV that is less than a predetermined voltage. In one specific instance, this predetermined voltage is less than or equal to 4 Kilovolts (kV). Additionally, objects or features with charge relaxation time constants of one second or less may also function as static dissipative features.

Once the configuration of the component specimen is completed, the component specimen may be integrated into a test panel, such as a flat test panel. The test panel may be configured so that it is large enough to incorporate a negative control region. The negative control region is an area on the test panel that generally produces a PBD when tested. The test panel may include regions in which thickness and/or area of the insulating coating between static dissipative features varies.

In some implementations, if static dissipative features on a particular conductive component cannot be moved, (such as due to the placement of the component in an overall assembly), it may be necessary to produce a component specimen with differing insulating coating surface areas and insulating coating thicknesses to determine the sensitivity of various configurations. For the purpose of repeating the test to verifying test result, a plurality of identical component specimens may be provided. In one instance, sufficient component specimens may be provided to permit at least 10 tests per configuration.

Figure 5:
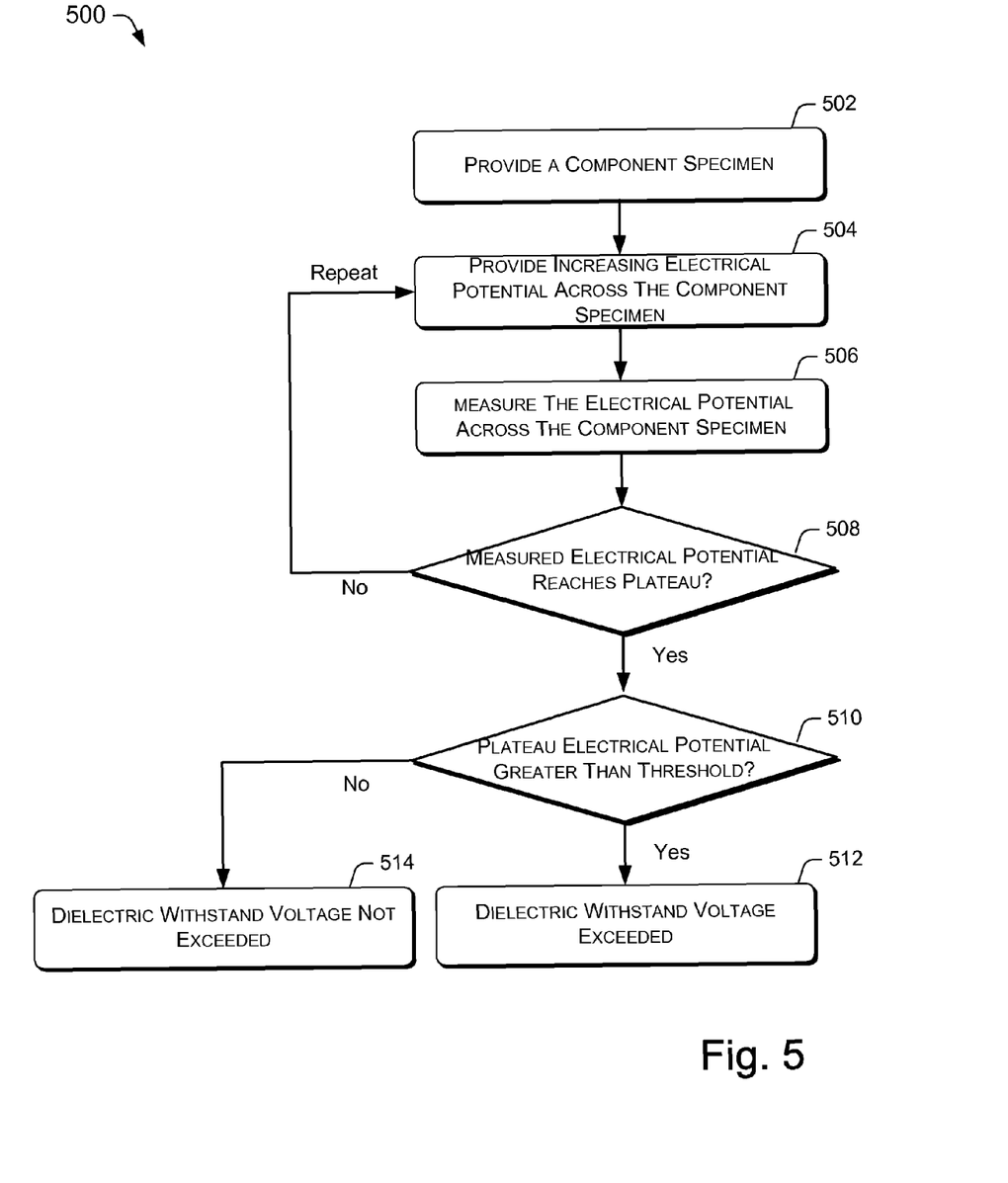
FIG. 5 is a flow diagram illustrating an exemplary process for determining the dielectric withstand voltage (DWV) for an insulating coating on a conductive component in accordance with an embodiment.

FIG. 5 illustrates an exemplary process 500 for determining the Dielectric Withstand Voltage (DWV) for an insulating coating on a conductive component. In certain embodiments, the conductive component may be a carbon fiber reinforced plastic (CFRP) component. Exemplary process 500 may be implemented using the exemplary DWV test system 200 shown in FIG. 2. However, it will be appreciated that the testing of an insulating coating on a CFRP component may be carried out using other electrical testing systems. For example, the testing may be conducted using procedures defined in ASTM 3755-97 as described above.

At block 502, a component specimen is provided for testing. The specimen may be a test sample that is representative of a conductive component with an insulating coating. The component specimen is illustrated as specimen 212 in FIG. 2 for exemplary purposes. In one implementation, the component specimen may be analyzed in the test bench 214 of the system 200. At block 504, a gradually increasing electrical potential relative to ground is introduced to the insulating component of the specimen. The increasing electrical potential may be supplied to the component specimen by first grounding at least one edge of the specimen to the conductive portion 218 of the test bench 214. In instances where the component specimen is a multi-layered CFRP sample, it may be necessary to ground each carbon fiber layer of the CFRP sample.

As shown in FIG. 9, this grounding may be accomplished by penetrating a CFRP sample 900 with a conductive member 902 (e.g., a metallic fastener). The CFRP sample 900 includes one or more resin layers 904 and one or more conductive carbon fiber matrix layers 906. The sample 900 also includes a non-conductive insulating coating layer 908. According to some implementations, the conductive member 902 penetrates each of the resin layers 904 and makes electrical contact with each of the conductive layers 906. The conductive member 902 is further grounded to a ground 910. The ground 910 may be conductive portion 218 of the DVW determination system 200 described in FIG. 2. Subsequently, the increasing electrical potential, as generated by the power supply 202, is applied to the specimen via the test cylinder 210. In one embodiment, the electrical potential generated by the power supply 202 may be gradually increased at a predefined rate, such as a rate of 500 Volts per second.

At block 506, the electrical potential applied to the specimen is measured. In some implementations, the measurement may be taken with the multi-meter 224 of the system 200. At decision block 508, a determination may be made as to whether the measured electrical potential (voltage) has reached a plateau in comparison to an increase in input electrical potential (e.g., the voltage measured using the multi-meter 224 set at "min hold" across the insulating layer no longer changes with increasing voltage from the power supply). If the measured electrical potential does not reach a plateau, ("no" at decision block 508), the process 500 may loop back to block 506, where the electrical potential is further increased at the gradual rate.

However, if it is determined that the measured electrical potential has reached a plateau, ("yes" at decision block 508), the process may continue to decision block 510. At decision block 510, it may be decided whether the measured electrical potential has exceeded a predetermined threshold. As describe above, the predetermined threshold is approximately 4 Kilovolts (kV). If the measured electrical potential does exceed the predetermined threshold ("yes" at decision block 510), it is concluded at block 512 that the DWV has been exceed. Nevertheless, if the measured electrical potential does not exceed the predetermined threshold ("no" at decision block 510), then it is concluded at block 514 that the DWV has not been exceeded. The process 500 may then return the DWV result to block 404 of the process 400.

Figure 6:
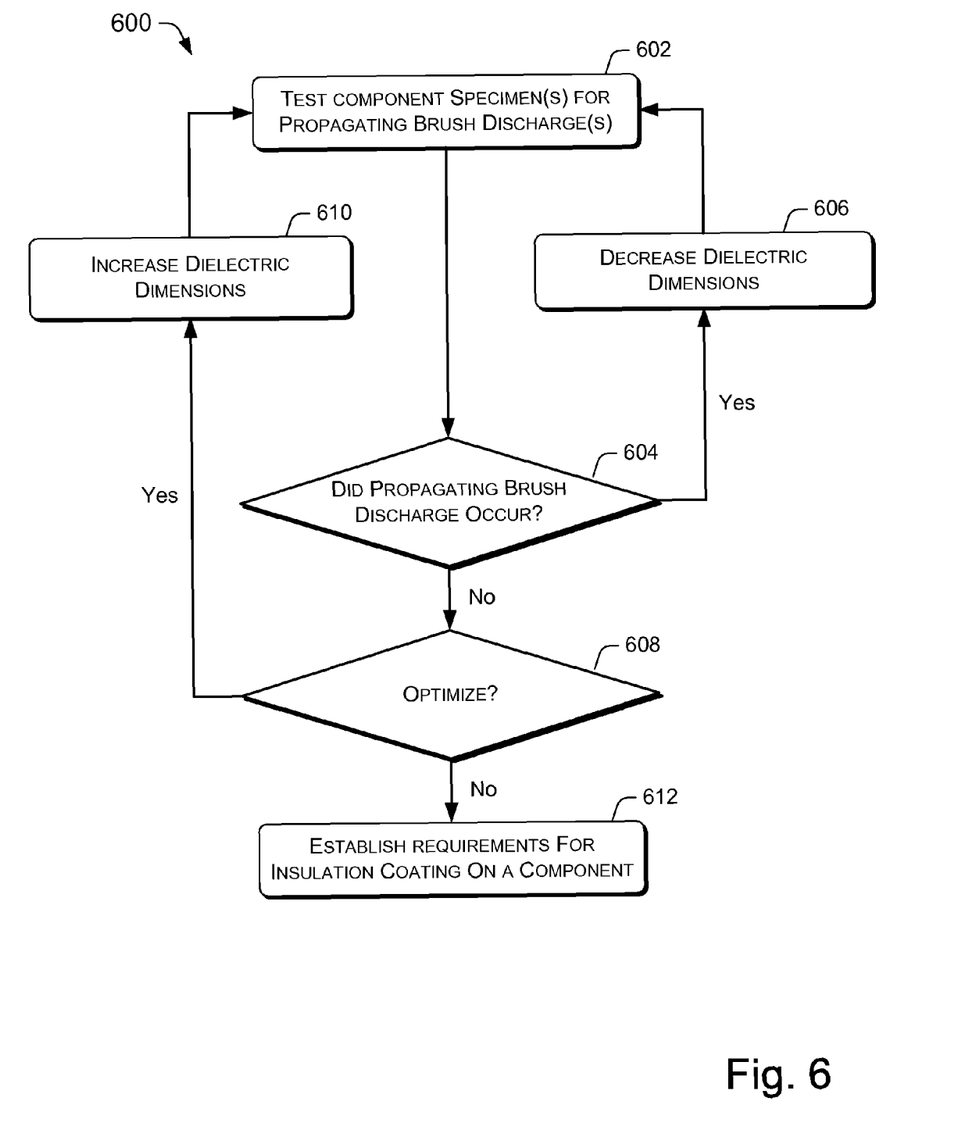
FIG. 6 is a flow diagram illustrating an exemplary process for determining the dimensions of insulation coating sections on a conductive component, in accordance with an embodiment.

FIG. 6 illustrates an exemplary process 600 for determining the dimensions of insulation coating sections on a conductive component. In certain embodiments, the conductive component may be a carbon fiber reinforced plastic (CFRP) component. The process 600 may be implemented on a propagating brush discharge (PBD) testing system, such as the exemplary system 300. At block 602, a specimen of the insulating coating covered conductive component is tested for propagating brush discharges. The component specimens may include the specimens described above with respect to FIG. 4. An exemplary propagating brush discharge testing procedure is illustrated in FIG. 7.

Figure 7:
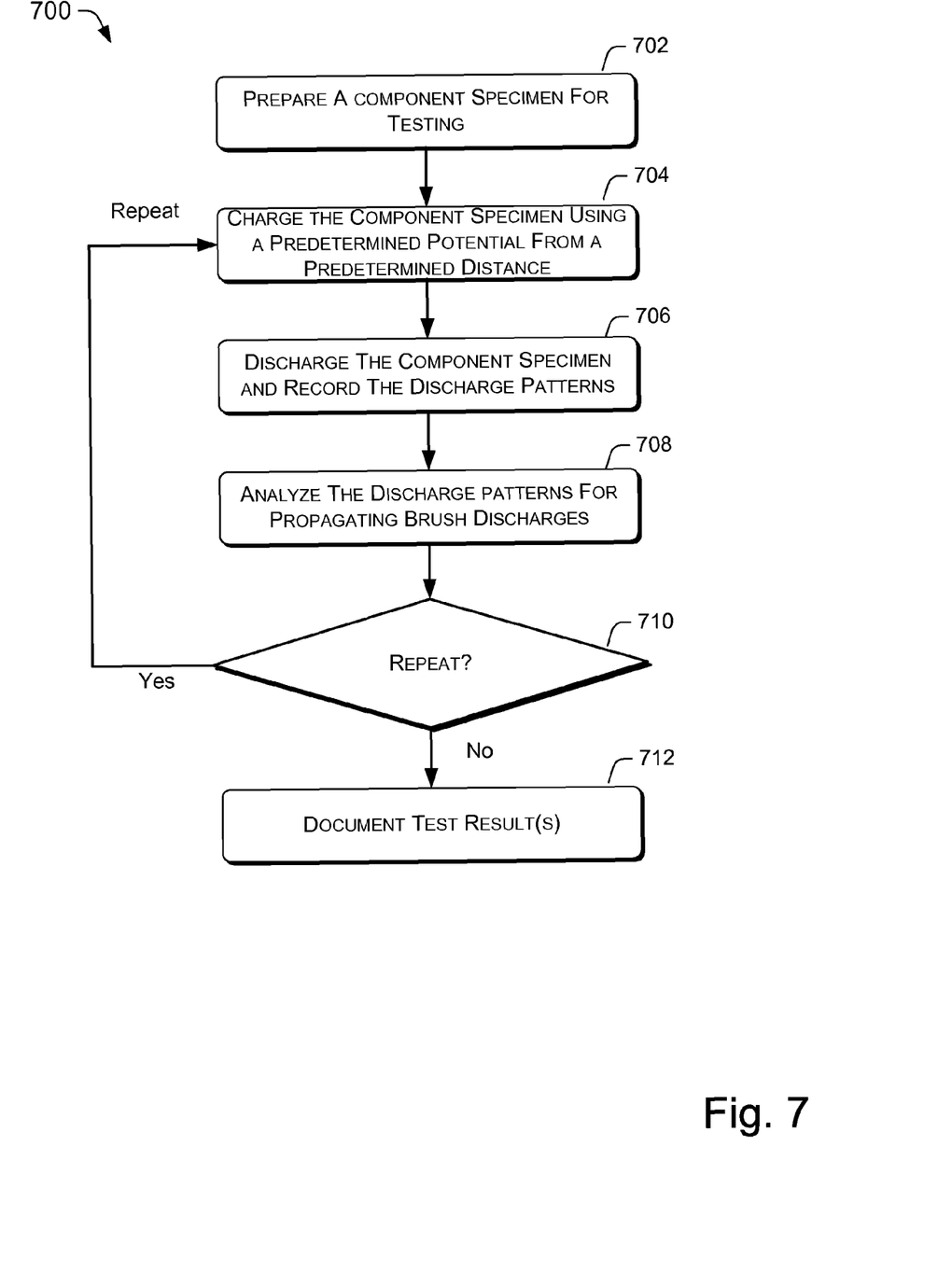
FIG. 7 is a flow diagram illustrating an exemplary process for determining the whether a conductive component with an insulating coating exhibits propagating brush discharges (PBD).

FIG. 7 illustrates an exemplary process 700 for determining the whether a insulating coating covered conductive component exhibits propagating brush discharges (PBD). In certain embodiments, the conductive component may be a carbon fiber reinforced plastic (CFRP) component. At block 702, a component specimen, such as the specimen 312, may be prepared for testing on the exemplary system 300 illustrated in FIG. 3. As described above, the component specimen may include a control area and one or more test regions, which are sections of varying insulating coating surface areas and insulating coating thicknesses on a component specimen. Exemplary test regions are illustrated as areas 1-9 on the specimen 312. Generally speaking, the component specimen may need to be cleaned and conditioned before the test is performed. For example, the component specimen may be cleaned with one of ethyl alcohol or isopropyl alcohol. The component specimen may be placed into a dehumidification chamber for drying. In one implementation, the component specimen may be dried for approximately 24 to 72 hours in a test chamber that has less than 25% relatively humidity (RH).

A system used to conduct the PBD test of the component specimen may also be prepared. In various embodiments, the electrical current output of the system 300 may be calibrated using a piece of a metallic plate. Specifically, by electrically connecting the power supply 302 and the measurement device 322 via the metallic plate, a "corona" current may be measured by the measurement device 322. Measurements may be repeated at 5 Kilovolts (kV) intervals up to approximately 30 Kilovolts (kV). In particular embodiments, the metallic plate may be a piece of aluminum alloy with an approximate dimension of 3"×6".

At block 704, an electrical charge is provided to the component specimen. In order to provide the electrical charge to the component specimen, the component specimen may be positioned on the test bench 314 of the system 300. As described above, the test bench 314 is located inside a test chamber 316 so that the atmospheric and humidity condition of the component specimen may be controlled during testing. Subsequently, at least one edge of the component specimen is connected to the conductive portion 318 of the test bench 314. As described above in reference to FIG. 9, in instances where the component specimen is a multi-layered CFRP specimen, it may be necessary to ground each carbon fiber layer of the CFRP specimen. In one implementation, this grounding may be accomplished by penetrating the carbon fiber layers with a conductive member (e.g., a metallic fastener), and then grounding the conductive member to the conductive portion 318. Following the grounding of the component specimen, the tip of the corona discharger 310 typically positioned off and at a predetermined height above the component specimen. For instance, the corona discharger 310 may be positioned approximately 1.5" to 1.75" above the specimen. Before initiating electrical potential application to the component specimen, the relative humidity level in the test chamber 316 is generally set to less than 30%, and typically 12%.

Subsequently, the output of power supply 302 is adjusted to a predetermined voltage. In one implementation, the predetermined voltage is approximately 20 to 30 Kilovolts (kV). However, it will be appreciated that in other implementations where the samples are thicker, the predetermined voltage may be higher. The tip of the corona discharger 310 is then moved around a test area of the component specimen in a methodical manner to "charge" the component specimen during the course of a predetermined duration. For example, the corona discharger 310 may be directed to produce "painting" movements over the component specimen. In some implementations, the predetermined duration may be approximately 30 seconds. During this charging process, the tip of the corona discharger 310 may exhibit a blue glow. After the component specimen has been charged for the predetermined duration, the tip of corona discharger 316 is moved off the specimen prior to terminating the output from the power supply. The removal of the tip prior voltage termination may advantageously prevent passive corona between the corona discharger 316 and the component specimen that can discharge the specimen.

At block 706, the component specimen is discharged and the discharge patterns are recorded using an image recorder, such as the image recorder 328 of the System 300. The discharge of the component specimen may be performed expediently so as to discharge the specimen at its most severely charged state. In various embodiments, the component specimen is discharged by a contact between a surface of the specimen and the discharge probe 326 of the system 300. While discharging the component, the characteristics of the discharges may also be recorded. These characteristics may include discharge frequency, discharge type, discharge size, and discharge intensity. In embodiments where the discharge probe 326 is electrically connected to the measurement device 322, the measurement device 322 may be used to quantify the amount of charge transfer (e.g., by integrating current or measuring charge). In specific instances, charge transferred to the probe 326 may be used to determine whether propagating brush discharges occurred.

The discharge of the component specimen may be performed multiple times provided charge remains on the area under test. Simultaneously, the patterns of the discharges may be captured using an image recorder, such as the image recorder 328 of the system 300, for subsequent analysis.

At block 708, the recorded discharge patterns may be analyzed for propagating brush discharges. For instance, the patterns may be analyzed according to the parameters outlined in Table I.

TABLE I

Parameters for Analyzing Discharge Patterns for Propagating Brush Discharges

| | |
|---|---|
| Lichtenberg pattern - less than approximately 2"-3" or greater in diameter | Propagating Brush Discharge (PBD) present |
| Lichtenberg pattern - approximately 2"-3" or less in diameter | PBD present |
| Discharge leaders (at least one) observed | PBD Present |
| Pinhole discharges | PBD Not Present |
| Brush discharges from specimen surface to the discharge probe | PBD Not Present |
| Spark discharges from the specimen surface to the discharge probe | PBD Not Present |
| Spark discharges from the specimen surface to an adjacent fastener | PBD Not Present |
| Edge glow where discontinuities exist on specimen surface | PBD Not Present |
| Back Corona ("sparkling effect") on specimen surface | PBD Not Present |

As shown in Table I, in various embodiments, the occurrence of propagating brush discharges is determined by the presence of one of the Lichtenberg patterns or the Lichtenberg discharge leaders in the recorded discharge patterns. However, it will be appreciated that in other embodiments, the occurrence of propagating brush discharges may also be determined based on one or more of the amount of charge transfer measured by the measurement device 322, as well as using other indicators.

At decision block 710, a determination may be made as to whether the test of the component specimen should be repeated. In particular implementations, the test may be repeated a plurality of times to verify the test results. If it is decided that the test should be repeated ("yes" at decision block 710), the process 700 may loop back to block 706, where another electrical potential application and discharge pattern analysis may be repeated via blocks 706-708. However, if it is decided that no additional test is necessary ("no" at decision block 710), the process 700 may proceed to block 712. At block 712, the test results relating to the occurrence of propagating brush discharges may be documented. The process 700 may then return to decision block 604 of process 600.

At decision block 604, a determination to dimension the insulating coating on a particular conductive component may be made based on whether propagating brush discharges occurred for the corresponding component specimen. If the propagating brush discharges did occur on the component specimen during test ("yes" at decision block 604), the process 600 may continue to block 606, where the insulating coating is dimensioned. According to various embodiments, the insulating coating may be dimensioned by decreasing the continuous surface area of the insulating coating, decreasing the thickness of the insulating coating, or decrease a combination thereof. For example, in reducing the continuous surface area of the insulating coating, at least one dimensional measurement, such as the length or width of the insulating coating on the component, may be reduced. Accordingly, the reduction in one of the dimensional measurement of the insulating coating results in smaller insulating coating covered surface area on the component. The smaller length or width, or the resultant smaller area may allow the surface charge present on the original insulating coating and component combination to dissipate, thereby preventing propagating brush discharges (PBD). In other examples, the propensity for propagating brush discharge from the insulating coating covered component may be mitigated by decreasing the thickness of the insulating coating disposed on the component. In one embodiment, the decrease in the surface area and/or the decrease in the thickness of the insulating coating may be achieved by producing one or more additional specimens that embody these modified measurements.

Figure 10A:
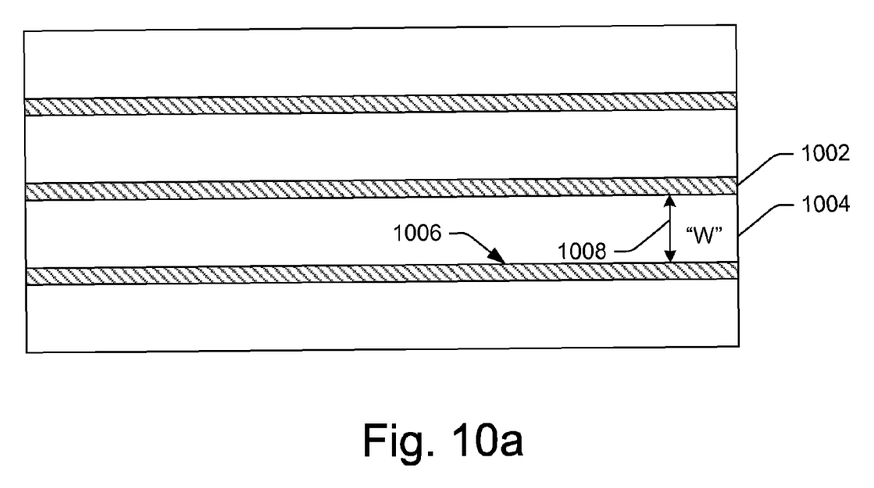
FIGS. 10a and 10b are plan views of insulating coatings on conductive components that may be modified to mitigate propagating brush discharges (PBD), in accordance with various embodiments.
Figure 10B:
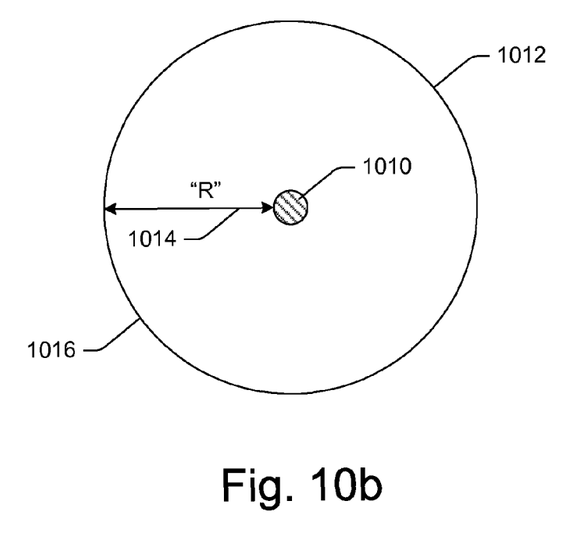

In still other embodiments, the insulating coating on a specimen may also be dimensioned by reducing a maximum distance any portion of the insulation coating may extend from an expected adjacent static dissipative feature. FIGS. 10*a* and 10*b* illustrate the reduction in this maximum distance for the purpose of dissipating surface charges to mitigate propagating brush discharges (PBD).

FIG. 10*a* shows a static dissipative feature 1002 that is adjacent an insulating coating section 1004. In this instance, the static dissipative feature 1002 is an unprimed area, that is, an uncoated surface of the component. According to various implementations, the reduction in the maximum distance may result in an edge 1006 of the insulating coating section 1004 (that is farthest from the unprimed area 1002) being moved closer to the static dissipative feature 1002. This is because the insulation coating section 1004 may no longer extend as far from the static dissipative feature 1002 when the maximum distance described above is reduced. In other words, a reduction in the maximum distance may result in a reduction in one or more dimensions, such as width "W" 1008, of the insulating coating section 1004.

Likewise, FIG. 10*b* shows a static dissipative feature 1010 that is adjacent an insulating coating section 1012. In this particular instance, the static dissipative feature 1010 may be a metallic fastener that provides electrical ground to the component. As illustrated, the insulating coating section 1012 may take the form of a circle with a radius "R" 1014 that extends from an edge of the circle 1016 to the static dissipative feature 1010. According to various implementations, the reduction in the maximum distance may result in the edge 1016 of the insulating coating section 1012 being moved closer to the static dissipative feature 1010. In other words, a reduction in the maximum distance may be results in a reduction in the radius "R" of the insulating coating section 1004, thereby shrinking the surface area covered by the insulating coating section 1012.

It will be appreciated that while the reduction of the maximum distance are illustrated above with respect to a rectangular insulation coating section 1002 and circular insulating coating section 1012, the insulation coating on the specimen may take any shape (e.g., oblong, trapezoidal, etc). Likewise, the maximum distance any portion of an insulation coating section may extend from the expected adjacent static dissipative feature may also be changed for these other shapes. The reduction to one or more dimensions of the insulation coating on a specimen, as resulting from a reduction in the maximum distance, may enable the surface charge present on the original insulating coating and component combination to dissipate, thereby mitigating propagating brush discharges (PBD).

Once the a new specimen has been dimensioned as described above, the process 600 may loop back to block 602, where the new specimen of the component with the modified insulating coating may be tested for propagating brush discharges. In this way, the insulating coating on the component may be continuously adjusted and tested.

However, if the propagating brush discharges did not occur on the component specimen during test illustrated in FIG. 7 ("no" at decision block 604), the process 600 may continue to decision block 608. At decision block 608, a determination may be made as to whether the one or more modifications (e.g., dimension reduction, thickness reduction) to the insulating coating should be optimized. If it is determined that the modifications are to be optimized, the process 600 may proceed to block 610.

At block 610, the dimensions of the insulating coating covering the component specimen may be further adjusted. Specifically, a component specimen with increased insulating coating surface area, increased insulating coating thickness, increased maximum distance at which any portion of the insulating coating may be from an adjacent static dissipative feature, or a combination thereof, may be produced for testing. For example, the surface area of the insulating coating covering the component may be increased, (e.g., by increase the length dimension and/or a width dimension on a new component specimen). Once the adjustment are made, the process may loop back to block 602, where a specimen of the component, incorporating the most recently adjusted insulating coating modifications, may be further tested for propagating brush discharges.

However, if it is determined that no additional optimization of the insulating coating on the component is needed ("no" at decision block 608, the process may advance directly to block 612. At block 612, the adjusted insulating coating surface dimensions and/or thickness may be implemented as requirements for dimensioning a surface coating on an actual conductive component. Accordingly, the insulating coating on the actual conductive component may be divided into discontinuous sections to prevent the build up of electrical charges. In some embodiments, the discontinuous sections of the insulating coating expose sections of one or more uncoated or bare surfaces of the conductive component. The conductive component with the dimensioned insulating coating may then be implemented in an application where propagating brush discharges were previously a concern.

Figure 8:
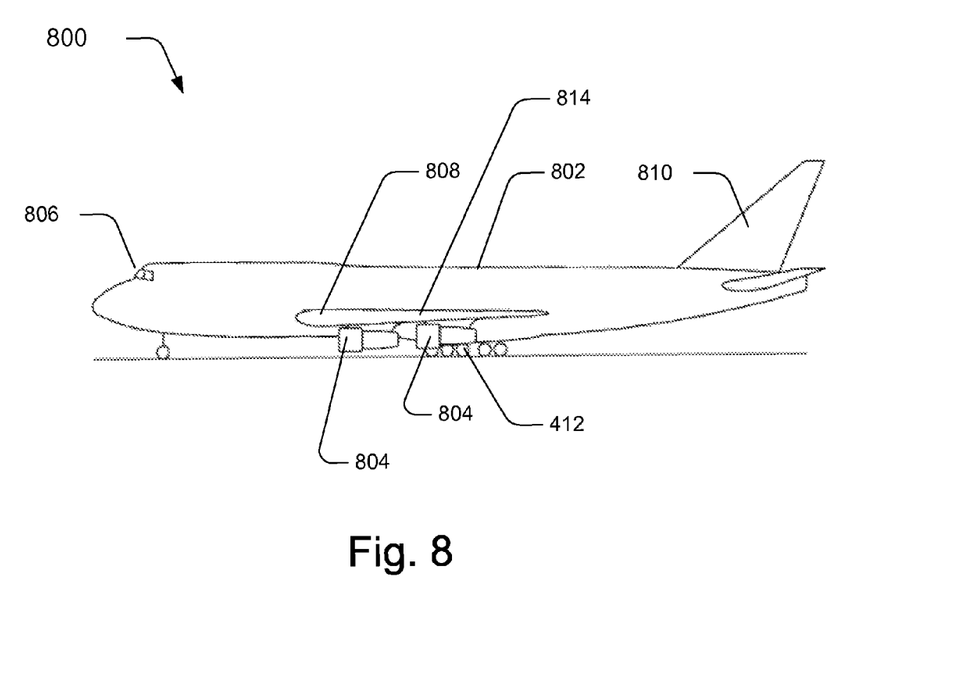
FIG. 8 is a side elevational view of an aircraft equipped with at least one CFRP component having an insulating coating prepared in accordance with the processes in FIGS. 4-7.

FIG. 8 is a side elevational view of an aircraft 800 in accordance with an embodiment. In general, except for one or more components in accordance with the present embodiment, the various components and subsystems of the aircraft 800 may be of known construction and, for the sake of brevity, will not be described in detail herein. As shown in FIG. 8, the aircraft 800 includes one or more propulsion units 804 coupled to a fuselage 802, a cockpit 806 in the fuselage 802, wing assemblies 808 (or other lifting surfaces), a tail assembly 810, a landing assembly 812, a control system (not visible), and a host of other systems and subsystems that enable proper operation of the aircraft 800. At least one carbon fiber reinforced plastic (CFRP) component 814 with an insulating coating dimensioned using the methods and system of this disclosure is located within at least one of the fuselage 402 or wing assemblies 808 of the aircraft 800.

Although the aircraft 800 shown in FIG. 8 is generally representative of a commercial passenger aircraft, including, for example, the 737, 747, 757, 767, 777, and 787 models commercially-available from The Boeing Company of Chicago, Ill., the inventive apparatus and methods disclosed herein may also be employed in the assembly of virtually any other types of aircraft. More specifically, the teachings of the present disclosure may be applied to the manufacture and assembly of other passenger aircraft, cargo aircraft, rotary aircraft, and any other types of aircraft, including those described, for example, in *The Illustrated Encyclopedia of Military Aircraft* by Enzo Angelucci, published by Book Sales Publishers, September 2001, and in *Jane's All the World's Aircraft* published by Jane's Information Group of Coulsdon, Surrey, United Kingdom, which texts are incorporated herein by reference. It may also be appreciated that other components dimensioned in accordance with the present disclosure may be utilized in other aerial vehicles.

Embodiments of systems and methods in accordance with the present disclosure may provide significant advantages over the prior art. The determination of maximum suitable dimensions for insulating coating sections may advantageously reduce the possibility of electrostatic buildup on a component by enabling static charges to escape to ground via uncoated sections of the component. At the same time, the dimensioned insulating coating sections may also prevent galvanic corrosion between the component and other galvanically incompatible components by enabling maximum insulating coating application.

While embodiments of the disclosure have been illustrated and described above, many changes can be made without departing from the spirit and scope of the disclosure. Accordingly, the scopes of the embodiments are not limited by the disclosure. Instead, the embodiments of the disclosure should be determined entirely by reference to the claims that follow.

What is claimed is:

1. A method for mitigating a propagating brush discharge from an insulating coating covered component, comprising:
   providing a carbon fiber reinforced plastic (CFRP) specimen that represents the component for testing, the CFRP specimen being at least partially covered by a non-conductive insulating coating section of a first surface area and a first thickness;
   conducting a test of the CFRP specimen for a propagating brush discharge that results from a capacitance charge in the specimen; and
   reducing at least one of the first surface area, the first thickness, a first distance to produce at least one of a second surface area, a second thickness, or a second distance when the CFRP specimen exhibits the propagating brush discharge,
   wherein the first distance is a maximum distance any portion of the non-conductive insulating coating section is located from an adjacent static dissipative feature.

2. The method of claim 1, further comprising increasing at least one of the first surface area, the first thickness, or the first distance to produce at least one of a third surface area, a third thickness, or a third distance when the CFRP specimen does not exhibit the propagating brush discharge.

3. The method of claim 2, further comprising:
   conducting another test of the CFRP specimen for an additional propagating brush discharge; and
   reducing at least one of the third surface area or the third thickness to produce at least one of a fourth surface area, a fourth thickness, or a fourth distance when the CFRP specimen exhibits the additional propagating brush discharge,
   wherein the fourth surface area is greater than the first surface area, and the fourth thickness is greater than the first thickness, and the fourth distance is less than the first distance.

4. The method of claim 3, further comprising establishing patterns for the non-conductive insulating coating on the component based on one of (1) at least one of the second surface area, the second thickness, or the second distance, (2) at least one of the third surface area, the third thickness, or the third distance, or (3) at least one of the fourth area, the fourth thickness, or the fourth distance.

5. The method of claim 1, further comprising:
   conducting another test of the CFRP specimen for an additional propagating brush discharge, the CFRP specimen including the non-conductive insulating coating section of at least one of the second surface area, the second thickness, or the second distance; and
   increasing at least one of the second surface area, the second thickness, or the second distance to produce at least one of a third surface area a third thickness, or a third distance when the CFRP specimen does not exhibit the additional propagating brush discharge,
   wherein the third surface area is less than the first surface area, the third thickness is less than the first thickness, and the third distance is greater than the first distance.

6. The method of claim 1, wherein the static dissipative features includes at least one of a bare component surface, a bare fastener, a pin hole that extends to the component, an insulating coating with a dielectric discharge voltage of less than or approximately 4 Kilovolts (kV), or another component with a charge relaxation time constants of one second or less.

7. The method of claim 1, further comprising determining a suitability of the component for a propagating brush discharge test prior to providing the CFRP specimen that represents the component for testing, wherein the determination is made based on at least one of a presence of a electric double layer on the component, a dielectric withstand voltage of the component, or a charge decay time constant of the non-conductive insulating coating section of the specimen.

8. The method of claim 7, wherein the electric double layer is present when the component is grounded, the non-conductive insulating coating is less than a predetermined maximum thickness, and the insulating coating is to separate the component from a source of electrostatic charge.

9. The method of claim 8, wherein the predetermined maximum thickness is 8-10 millimeters.

10. The method of claim 7, the dielectric withstand voltage of the component is determined based on a measured voltage plateau of the component during the application of an increasing electrical potential to the component.

11. The method of claim 7, wherein determining a suitability of the component includes determining that the component is suitable for a propagating brush discharge test when at least one of an electric double layer is present on the component, a dielectric withstand voltage of the components exceeds a predetermined voltage threshold, or the charge decay time constant of the non-conductive insulating coating section is greater than approximately one second.

12. The method of claim 11, wherein the predetermined voltage threshold is approximately 4 Kilovolts.

13. The method of claim 1, wherein conducting a test includes conducting a test of the CFRP specimen for the propagating brush discharge at a relative humidity of less than 30%.

14. The method of claim 1, wherein conducting the test of the CFRP specimen for the propagating brush discharge includes:
  Discharging the CFRP specimen that was charged from a predetermined distance; and
  determining an occurrence of the propagating brush discharge based on the corresponding discharge pattern produced by the propagating brush discharge.

15. The method of claim 14, wherein conducting the test of the specimen for the propagating brush discharge further includes drying the CFRP specimen for 24 to 72 hours at less than 25% relatively humidity prior to discharging the specimen.

16. The method of claim 14, wherein the predetermined distance is 1.5 inches to 1.75 inches.

17. The method of claim 14, wherein determining the occurrences of the propagating brush discharge includes determining that propagating brush discharge occurred when the one or more discharge patterns includes at least one of a Lichtenberg pattern or a Lichtenberg discharge leader.

18. A method for propagating brush discharge testing, comprising:
  discharging a carbon fiber reinforced plastic (CFRP) specimen that was charged from a predetermined distance, the CFRP specimen being at least partially covered by a non-conductive insulating coating section of a first surface area and a first thickness; and
  observing a discharge pattern from the CFRP specimen for at least one of a Lichtenberg pattern or a Lichtenberg discharge leader of a propagating brush discharge;
  reducing at least one of the first surface area, the first thickness, a first distance to produce at least one of a second surface area, a second thickness, or a second distance when the CFRP specimen exhibits the at least one of the Lichtenberg pattern or the Lichtenberg discharge leader of the propagating discharge;
  increasing at least one of the first surface area, the first thickness, or the first distance to produce at least one of a third surface area, a third thickness, or a third distance when the CFRP specimen does not exhibit the at least one of the Lichtenberg pattern or the Lichtenberg discharge leader of the propagating brush discharge,
  wherein the first distance is a maximum distance any portion of the non-conductive insulating coating section is located from an adjacent static dissipative feature.

* * * * *